United States Patent
Assell et al.

(10) Patent No.: US 11,969,174 B2
(45) Date of Patent: Apr. 30, 2024

(54) BONE FUSION SYSTEM

(71) Applicant: ForCyte Medical, LLC, Marietta, GA (US)

(72) Inventors: Robert Assell, Minneapolis, MN (US); Andy Freeman, Minneapolis, MN (US)

(73) Assignee: Forcyte Medical, LLC, Marietta, GA (US)

( * ) Notice: Subject to any disclaimer, the term of this patent is extended or adjusted under 35 U.S.C. 154(b) by 0 days.

(21) Appl. No.: 18/102,451

(22) Filed: Jan. 27, 2023

(65) Prior Publication Data

US 2023/0165593 A1   Jun. 1, 2023

Related U.S. Application Data

(62) Division of application No. 17/179,036, filed on Feb. 18, 2021, now Pat. No. 11,696,771.

(Continued)

(51) Int. Cl.
*A61B 17/16*   (2006.01)
*A61F 2/46*   (2006.01)
(Continued)

(52) U.S. Cl.
CPC ...... *A61B 17/1633* (2013.01); *A61B 17/1615* (2013.01); *A61B 17/1628* (2013.01);
(Continued)

(58) Field of Classification Search
CPC . A61B 17/16; A61B 17/1615; A61B 17/1628; A61B 17/1631; A61B 17/1633;
(Continued)

(56) References Cited

U.S. PATENT DOCUMENTS 5,269,785 A * 12/1993 Bonutti ............... A61B 10/025
                                                   606/167
5,624,418 A    4/1997 Shepard
(Continued)

FOREIGN PATENT DOCUMENTS

EP   2704647 B1 *  8/2016  ............. A61B 17/16
EP   2822482 B1 * 12/2017  ............. A61B 17/16
(Continued)

OTHER PUBLICATIONS

International Search Report and Written Opinion received for PCT Serial No. PCT/US2021/018570 on May 7, 2021, 9 pages.
Office Action dated Nov. 16, 2021 for U.S. Appl. No. 16/413,461.

*Primary Examiner* — Eric S Gibson
(74) *Attorney, Agent, or Firm* — Spencer Fane, LLP

(57) ABSTRACT

A bone fusion system including a collection vessel, an abrading and harvesting device, tubing and a probe. The abrading and harvesting device includes a needle portion and a sharpened tip. The needle portion has a central bore extending therethrough. The needle portion has a distal end. The sharpened tip is attached to the distal end of the needle portion. The tubing is operably connecting the collection vessel and the abrading and harvesting device. The probe has a threaded portion and a tip portion at a distal end of the threaded portion. The threaded portion has a thread on an outer surface thereof. The tip portion is unsharpened and does not have a thread on an outer surface thereof. The probe is extendible through the central bore.

20 Claims, 4 Drawing Sheets

Related U.S. Application Data

(60) Provisional application No. 62/978,343, filed on Feb. 19, 2020.

(51) Int. Cl.
*A61B 17/34* (2006.01)
*A61F 2/30* (2006.01)

(52) U.S. Cl.
CPC ........ *A61F 2/4601* (2013.01); *A61B 17/1664* (2013.01); *A61B 2017/3454* (2013.01); *A61B 2217/005* (2013.01); *A61F 2002/30622* (2013.01); *A61F 2002/30995* (2013.01)

(58) Field of Classification Search
CPC ............ A61B 17/1635; A61B 17/1659; A61B 17/1664; A61B 17/1671; A61B 17/8897; A61B 2/46; A61B 2/4601; A61B 2/4644; A61F 2002/30622; A61F 2002/30995
See application file for complete search history.

(56) References Cited

U.S. PATENT DOCUMENTS

| | | | | |
|---|---|---|---|---|
| 8,109,919 B2* | 2/2012 | Kraft | A61B 10/025 604/35 |
| 8,579,912 B2* | 11/2013 | Isaza | A61B 17/1742 606/86 R |
| 9,101,371 B2* | 8/2015 | Assell | A61B 17/1664 |
| 9,119,732 B2* | 9/2015 | Schifano | A61B 17/8872 |
| 9,149,283 B2* | 10/2015 | Assell | A61B 17/320016 |
| 9,161,763 B2* | 10/2015 | Assell | A61B 17/16 |
| 9,662,124 B2* | 5/2017 | Assell | A61B 17/1617 |
| 9,713,478 B2* | 7/2017 | Assell | A61F 2/30988 |
| 10,363,140 B2* | 7/2019 | Mauldin | A61B 17/1604 |
| 10,596,002 B2* | 3/2020 | Assell | A61B 17/84 |
| 11,173,036 B2* | 11/2021 | Assell | A61B 17/320016 |
| 11,278,336 B2* | 3/2022 | Assell | A61B 17/8822 |
| 11,337,710 B2* | 5/2022 | Assell | A61M 1/79 |
| 11,602,588 B2* | 3/2023 | Assell | C12M 45/00 |
| 11,696,771 B2* | 7/2023 | Assell | A61F 2/4644 606/80 |
| 2003/0225364 A1* | 12/2003 | Kraft | A61B 10/025 604/95.04 |
| 2006/0273049 A1 | 12/2006 | Leach | |
| 2008/0283474 A1 | 11/2008 | Leach | |
| 2009/0014391 A1 | 1/2009 | Leach | |
| 2009/0287190 A1 | 6/2009 | Shippert | |
| 2013/0030456 A1* | 1/2013 | Assell | A61B 17/32002 606/170 |
| 2013/0197590 A1* | 8/2013 | Assell | A61B 17/1671 606/300 |
| 2014/0277460 A1* | 9/2014 | Schifano | A61B 17/8605 606/86 R |
| 2014/0323914 A1 | 10/2014 | VanderWoude | |
| 2015/0110890 A1 | 4/2015 | Assell | |
| 2015/0182268 A1* | 7/2015 | Donner | A61B 17/8872 606/291 |
| 2015/0273360 A1 | 10/2015 | King | |
| 2015/0327872 A1* | 11/2015 | Assell | A61B 17/16 606/279 |
| 2016/0128838 A1* | 5/2016 | Assell | A61B 17/320016 623/17.11 |
| 2016/0325018 A1* | 11/2016 | Assell | A61B 17/8805 |
| 2016/0331878 A1 | 11/2016 | McGillicuddy | |
| 2017/0007409 A1* | 1/2017 | Mauldin | A61B 17/0218 |
| 2017/0296346 A1* | 10/2017 | Assell | A61B 17/1617 |
| 2018/0353206 A1* | 12/2018 | Assell | A61B 17/3472 |
| 2019/0125538 A1* | 5/2019 | Assell | A61B 17/1671 |
| 2019/0381285 A1* | 12/2019 | Althoff | A61M 25/09041 |
| 2020/0222195 A1* | 7/2020 | Assell | A61B 17/84 |
| 2021/0251638 A1* | 8/2021 | Assell | A61B 17/1659 |
| 2022/0022912 A1* | 1/2022 | Efremkin | A61B 17/320725 |
| 2022/0071770 A1* | 3/2022 | Assell | A61B 17/16 |
| 2023/0165593 A1* | 6/2023 | Assell | A61B 17/1631 606/80 |

FOREIGN PATENT DOCUMENTS

| | | | | |
|---|---|---|---|---|
| WO | WO-2012151573 A1 * | 11/2012 | ............ | A61B 17/16 |
| WO | WO-2013138655 A1 * | 9/2013 | ............ | A61B 17/16 |
| WO | WO-2021168107 A1 * | 8/2021 | ........ | A61B 17/1615 |

* cited by examiner

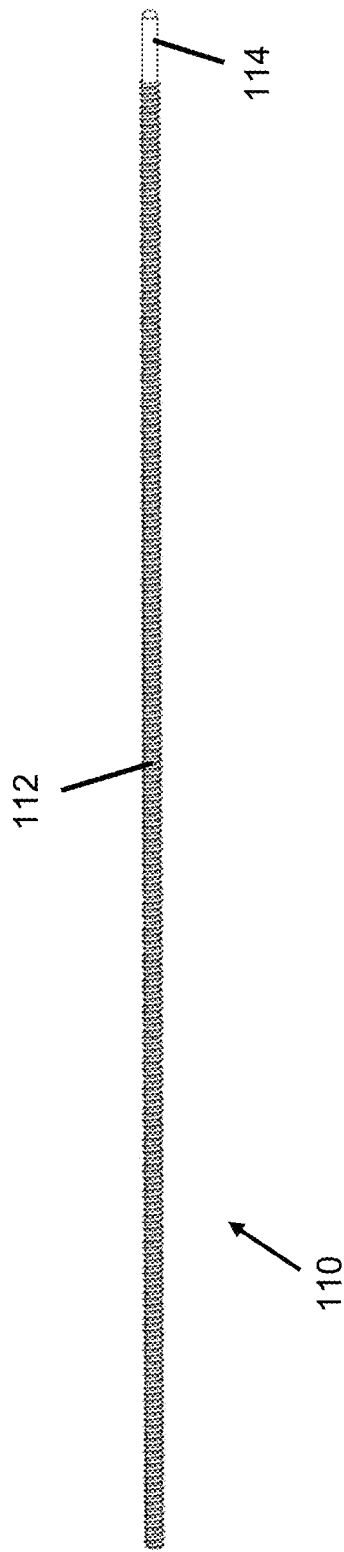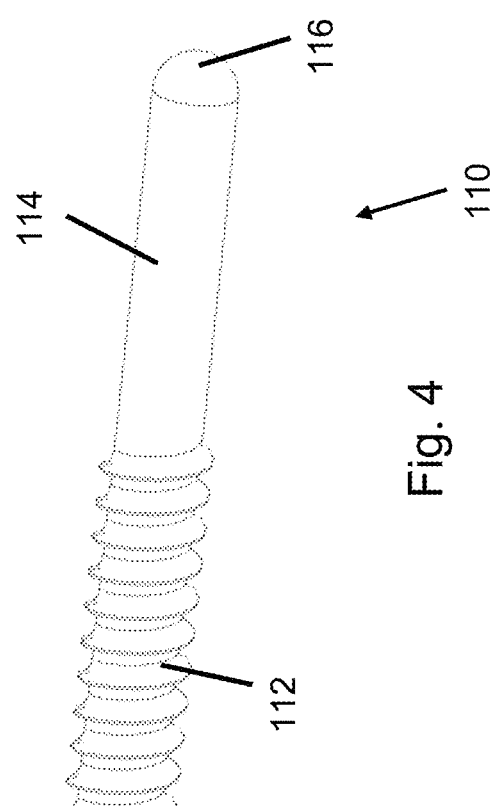

BONE FUSION SYSTEM

REFERENCE TO RELATED APPLICATION

This application is a divisional of U.S. application Ser. No. 17/179,036, filed Feb. 18, 2021, and claims priority to Provisional Applic. No. 62/978,343, filed on Feb. 19, 2020, the contents of which are incorporated herein by reference.

FIELD OF THE INVENTION

The invention relates generally to processes for treating joint ailments. More particularly, the invention relates to a systems and methods for causing fusion of the sacroiliac joint.

BACKGROUND OF THE INVENTION

In certain situations, the sacroiliac joint degrades in a person such that there is significant pain to the person. One technique that is used to eliminate or reduce the sacroiliac pain is to fuse the sacroiliac joint such as by inserting a fixation device that extends between the sacrum and the ilium.

The likelihood of success of the sacroiliac fusion may be enhanced by exposing bleeding bone on the adjacent surfaces of the sacrum and the ilium. One device and technique that has been used to form the bleeding bone on the adjacent surfaces of the sacrum and the ilium is an undercutting system that is inserted through the aperture in which the fixation device is to be inserted.

A limitation is that the undercutting system must be small enough to fit through the aperture in the ilium and the cutting element needs to deflect from an orientation aligned with the axis of the aperture to an orientation that is generally perpendicular to the axis of the aperture between the sacrum and the ilium while having sufficient strength to cut through the surfaces of the sacrum and the ilium to produce bleeding bone.

Others have proposed a lateral approach in which a cutter is inserted between the surfaces of the sacrum and the ilium. This approach has challenges because the surfaces of the sacrum and the ilium are generally not planar.

SUMMARY OF THE INVENTION

An embodiment of the invention is directed to a method of fusing a first bone and a second bone. An abrading and harvesting device is provided that includes a needle portion having a sharpened tip. The needle portion has a central bore extending therethrough. The needle portion has a proximal end and a distal end. The sharpened tip is attached to the distal end of the needle portion. A probe is provided having an unsharpened tip portion. The probe is extended between the first bone and the second bone. The needle portion is extended over the probe by passing the proximal end of the probe through the central bore. The first bone and the second bone are abraded with the sharpened tip to cause bleeding bone to be exposed on the first bone and the second bone. A device is placed along a path formed by the needle portion between the first bone and the second bone.

Another embodiment of the invention is directed to a bone fusion system that includes a collection vessel, an abrading and harvesting device, tubing and a probe. The abrading and harvesting device includes a needle portion and a sharpened tip. The needle portion has a central bore extending therethrough. The needle portion has a distal end. The sharpened tip is attached to the distal end of the needle portion. The tubing operably connects the collection vessel and the abrading and harvesting device. The probe has an unsharpened tip. The probe is extendible through the central bore.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 3 is a side view of a probe for use with the bone fusion system.

FIG. 4 is an enlarged view of a distal end of the probe of FIG. 3.

DETAILED DESCRIPTION OF THE INVENTION

Figure 1:
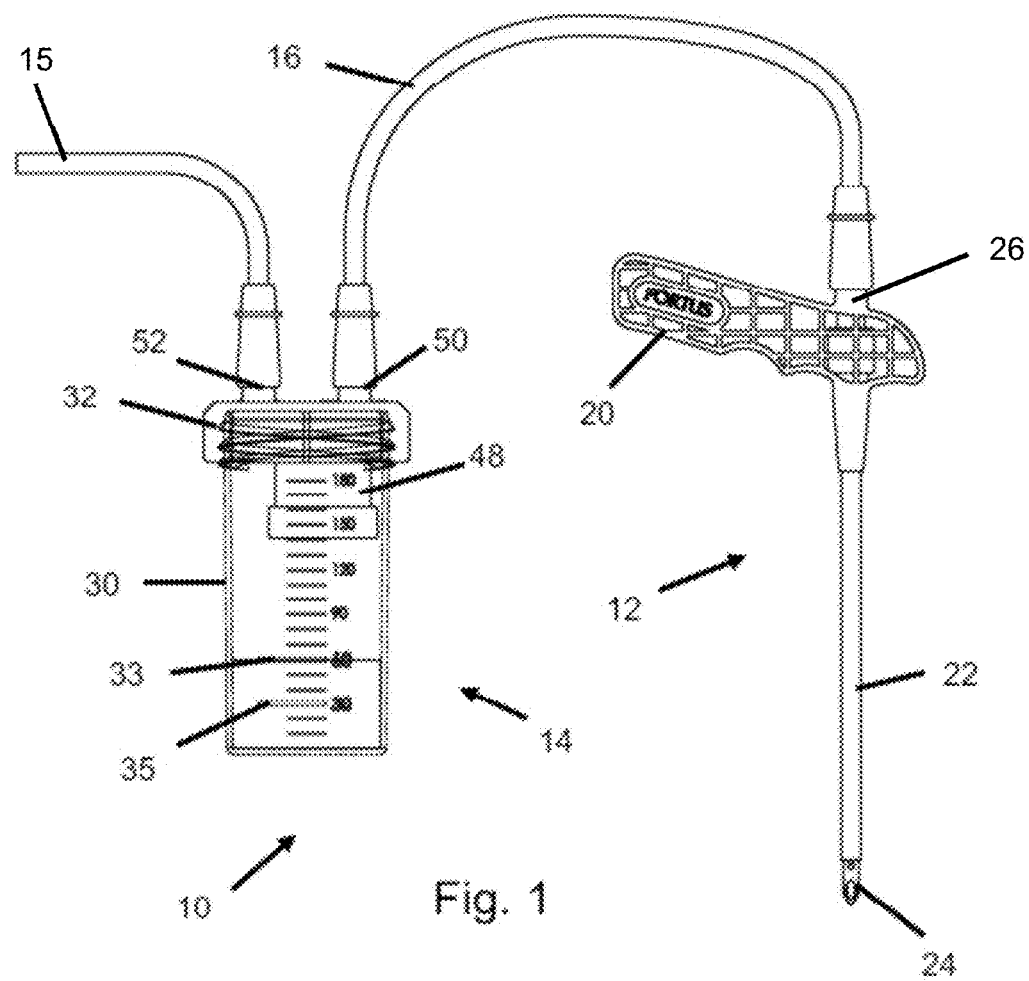
FIG. 1 is a side view of a bone fusion system according to an embodiment of the invention.

An embodiment of the invention is directed to a system for fusing two adjacent bones, which is illustrated in the figures. In certain embodiments, the invention is used in conjunction with sacroiliac fusion. In other embodiments, the invention is used in conjunction with anterior cervical discectomy and fusion. In still other embodiment, the invention is used in conjunction with triple arthrodesis.

The bone fusion system 10 generally includes an abrading and harvesting device 12 that is operably attached to a tissue processing device 14 with tubing 16. The bone fusion system 10 also includes a probe 110. In certain embodiments, the probe 110 includes threads on at least a portion of an outer surface thereof.

The bone fusion system 10 facilitates exposing bleeding bone on the adjacent surfaces of the sacrum and the ilium to facilitate sacroiliac fusion, as is described in more detail herein. The bone fusion system 10 also facilitates the recovery of tissues and bone fragments that can be used to facilitate fusion.

A significant advantage of the invention is that it is a contained system, which facilitates use of the invention in an operating room. The invention thereby enables treatment products to be prepared using materials aspirated from the patient in a cost-effect manner proximate to when it is desired to use the treatment products. The invention thereby provides a completely autologous process that enables use of the patient's own tissue in preparing treatment products.

The abrading and harvesting device 12 includes a handle portion 20 and a needle portion 22 that are operably connected to each other. In certain embodiments, the needle portion 22 is detachably connected to the handle portion 20. In other embodiments, the needle portion 22 is integrally formed with the handle portion 20.

In certain embodiments, the needle portion 22 may have an outer diameter of about 6 millimeters. A central bore 23 extends through the needle portion 22. Forming the needle portion 22 with this diameter minimizes the potential that bone fragments will become stuck while being drawn through the needle portion 22 during the aspiration process.

The needle portion 22 having the preceding characteristics may have a two-part configuration that includes a shaft portion and a tip portion 24. The shaft portion may include an inner shaft and an outer shaft. The inner shaft may be fabricated from a metallic material such as stainless steel. The metallic material thereby provides the needle portion 22 with a relatively high strength while having a relatively thin wall thickness.

In certain embodiments, the wall thickness of the metallic material may be less than about 10 thousandths of an inch. In certain embodiments, the wall thickness of the inner shaft is between about 3 and 6 thousandths of an inch. In still other embodiments, the wall thickness of the inner shaft is about 4 thousandths of an inch.

Fabricating the inner shaft with a relatively thin wall thickness allows the inner channel to be relatively wide to facilitate a large flow rate of tissue (and potentially bone fragments) therethrough while at the same time having a relatively small outer diameter.

The outer shaft may be fabricated from a polymeric material that is molded over the inner shaft. The outer shaft thereby enhances strength of the inner shaft while allowing the needle portion 22 to deflect during the process of extending the needle portion 22 between the ilium and the sacrum.

In another embodiment, the needle portion 22 is fabricated from a spiral wound wire that is coated with a material such as plastic. In certain embodiments, there may be more than one spiral wound wire. For example, there may be two spiral wound wires that are wound in opposite directions. Forming the needle portion 22 with this configuration may increase the flexibility of the needle portion 22 so that the needle portion 22 more readily deflects to conform to the non-planar surfaces of the sacrum and the ilium.

In still another embodiment, the needle portion 22 is fabricated from a material with a relatively low bending stiffness so that the needle portion 22 deflects when being extended between the sacrum and the ilium in response to changes in the orientation of the sacrum and the ilium. An example of a material having these characteristics is PEEK.

Because of the limited distance at which the needle portion 22 is inserted between the sacrum and the ilium, it is not necessary for the entire length of the needle portion 22 to have enhanced flexibility. Rather, only the part of the needle portion 22 that extends between the sacrum and the ilium may have enhanced flexibility.

To provide the needle portion 22 with a desired level of sharpness, the needle portion 22 has the tip portion 24 that is fabricated from a metallic material as the metallic material provides an enhanced sharpness as compared to a tip fabricated from a polymeric material. The tip portion 24 may be attached to the distal end of the inner tube before the outer tube is molded over the inner tube.

Figure 2:
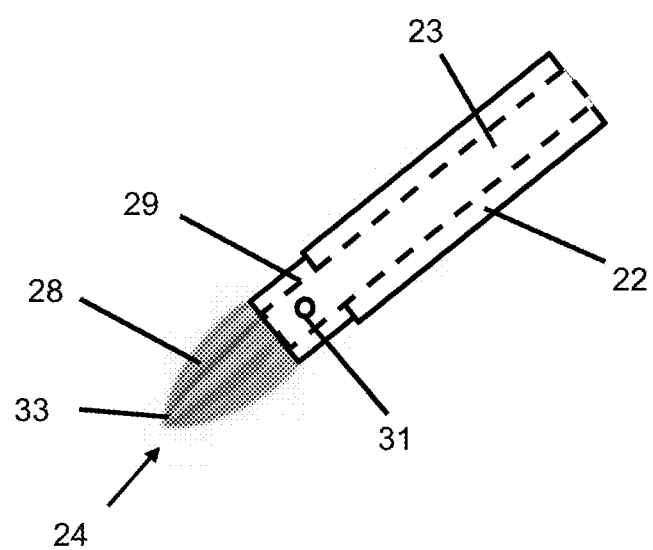
FIG. 2 is a perspective view of a needle for use in conjunction with the bone fusion system of FIG. 1.

The tip portion 24, which is most clearly illustrated in FIG. 2, facilitates disrupting the surface of the sacrum and the ilium to form the bleeding bone. One suitable tip configuration has a fluted design as illustrated in FIG. 2. At least a portion of the flutes has a sharpened surface or ridge 28.

The sharpened surface 28 facilitates cutting while the needle portion 22 is inserted between the sacrum and the ilium. The sharpened surface 28 also facilitates cutting tissue while the needle portion 22 is axially rotated.

Intermediate the tip portion 24 and the needle portion 22, a reduced diameter region 29 may be provided. The reduced diameter region 29 may have an outer diameter that is less than an outer diameter of the needle portion 22 that is adjacent thereto. The reduced diameter region 29 may also have an outer diameter that is less than an outer diameter of the tip portion 24.

Using this structure facilitates forming a seal between the outer surface of the needle portion 22 and the tissue adjacent thereto. This configuration also facilitates flow of tissue from the tip portion 24 to the reduced diameter region 29 such that the tissue may be extracted through an aperture 31 in the reduced diameter region 29 that is in communication with the central bore 23 that extends along a length of the needle portion 22.

There may be multiple apertures 31 provided on the device to enhance the rate at which the tissue can be withdrawn from the patient. Multiple apertures 31 may also minimize the potential of the aspiration process being interrupted by plugging of a significant portion of the apertures 31.

The tissue processing device 14 generally includes a collection vessel 30 to which a collection vessel cap 32 is operably attached as illustrated in FIG. 1. The collection vessel 30 may be formed with a size based upon the volume of tissue that is anticipated to be aspirated from the patient. In certain embodiments, the collection vessel 30 has a volume of about 180 cubic centimeters.

The collection vessel 30 may have a variety of shapes using the concepts of the invention. In certain embodiments, the collection vessel 30 has a generally cylindrical shape. Using such a shape enables the collection vessel cap 32 to be attached using a rotational motion.

A side of the collection vessel 30 may include at least two volume collected markers 33, 35. In one embodiment, the volume collected markers include an upper marker 33 and a lower marker 35. The upper marker 33 and the lower marker 35 thereby provide guidance to the person using the invention regarding whether a desired volume of tissue has been collected. In other embodiments, the volume collected markers may include a series of identifiers that correspond to a conventional volume measuring system such as milliliters.

Proximate an upper end of the collection vessel 30, an opening may be provided. In one such embodiment, the opening is generally circular and has a thread on a surface thereof that can be used when attaching the collection vessel cap 32 to the collection vessel 30. In certain embodiments, the thread may be on an outer surface of the opening. A person of skill in the art will appreciate that a variety of other techniques may be used to attach the collection vessel cap 32 to the collection vessel 30.

One aspect of the attachment of the collection vessel cap 32 to the collection vessel 30 is that a substantially air-tight seal is formed when the collection vessel cap 32 is attached to the collection vessel 30 so that a vacuum may be used to draw the aspirated tissue into the collection vessel 30.

The collection vessel 30 may be fabricated from a variety of materials using the concepts of the invention. In one embodiment, at least a portion of the collection vessel 30 is fabricated from a transparent material. Such a configuration enables a person using the bone fusion system 10 to not only view the volume of aspirated tissue and bone fragments in the collection vessel 30 but also other characteristics of the aspirated tissue and bone fragments such as a color of the aspirated tissue and/or the presence of discrete regions in the aspirated tissue.

Another criterion for the material that is used in fabricating the collection vessel 30 is that the material be biologically compatible and facilitate sterilization of the collection vessel 30 prior to use. An example of one such material that may be used to fabricate the collection vessel 30 is polycarbonate.

The collection vessel cap 32 may have a generally cylindrical configuration with an inner diameter that is selected based upon an outer diameter of the collection vessel 30 proximate the threaded region to facilitate removable attachment of the collection vessel cap 32 to the collection vessel 30. In this regard, the collection vessel cap 32 may include a thread on an inner surface thereof that is shaped generally complementary to the thread on the collection vessel 30.

While not illustrated, at least a portion of the outer surface of the collection vessel cap 32 may have a shape and/or texture that enhances the ability to grasp the collection vessel cap 32 and turn the collection vessel cap 32 with respect to the collection vessel 30. Because of the nature of the invention and the potential desire to remove the collection vessel cap 32, the collection vessel cap 32 is typically intended to be tightened and loosened using manual force.

The collection vessel cap 32 includes a first port 50 and a second port 52 formed therein. A person of skill in the art will appreciate that at least one of the first port 50 and the second port 52 may alternatively be formed in the collection vessel 30.

The first port 50 includes a connector that facilitates attachment to the tubing 16. In certain embodiments, the first port 50 enables tubing 16 to be attached and detached. When the tubing 16 is attached, a substantially gas-impervious seal is formed. The first port 50 may include a standardized connector profile that enables a variety of objects to be attached thereto. An example of one suitable standardized connector is marketed under the identifier Leur Lock.

Similar to the first port 50, the second port 52 may be formed with a standardized connector profile. An example of one such connector profile that can be used for the second port 52 is a tapered push-on connector that facilitates a friction connection. In certain embodiments, the push-on connector includes a plurality of ridges, which reduce the potential of the tubing or other object becoming detached from the second port 52. In certain embodiments, the second port 52 enables tubing 15 to be attached and detached. When the tubing 15 is attached, a substantially gas-impervious seal is formed.

The collection vessel cap 32 may be fabricated from a variety of materials using the concepts of the invention. In one embodiment, at least a portion of the collection vessel cap 32 is fabricated from a transparent material.

Another criterion for the material that is used in fabricating the collection vessel cap 32 is that the material be biologically compatible and facilitate sterilization of the collection vessel cap 32 prior to use. An example of one such material that may be used to fabricate the collection vessel cap 32 is acrylonitrile butadiene styrene.

A filter container 48 may be provided with respect to the tissue processing device 14 for separating bone fragments from the other aspirated tissue. The filter container 48 is positioned so that before the bone fragments and tissue flow into the collection vessel 30, these components pass through the filter container 48. The filter container 48 thereby facilitates separation of the bone fragments from the other portions of the aspirated tissue.

In certain embodiments, the filter container 48 is attached to an inner surface of the collection vessel cap 32. The filter container 48 may be removably attached to the collection vessel cap 32 such as using a threaded mechanism.

In other embodiments, the filter container 48 may be attached to an outer surface of the collection vessel cap 32. In such an embodiment, the first port 50 may be directly attached to the filter container 48. In still other embodiments, the filter container 48 may be separate from the tissue processing device 14. In this configuration, the tubing 16 is attached to the filter container 48. Another section of tubing (not shown) attached the filter container outlet to the first port 50.

The filter container 48 may have a volume that is significantly smaller than the volume of the tissue processing device 14. In certain embodiments, the filter container 48 has a volume of less than about 20 cubic centimeters. In other embodiments, the filter container 48 has a volume of about 15 cubic centimeters.

A surface of the filter container 48 may have perforations formed therein. In certain embodiments, a lower surface of the filter container 48 may be perforated having a plurality of openings formed therein. The size of the openings may be selected to retain substantially all of the bone fragments in the filter container 48 as the bone fragments and tissue are aspirated from the patient. On the other hand, the openings are sufficiently large so that the aspirated liquid is permitted to flow through the lower surface and into the collection vessel 30. The perforations thereby affect physical separation of the aspirate.

In certain embodiments, the lower surface is integrally formed with the other components of the filter container 48. In other embodiments, the lower surface may be removably attached to the filter container 48 such as using a threaded mechanism. This threaded mechanism may be similar to the threaded mechanism that is used to attach the filter container 48 to the collection vessel cap 32.

A filter material may at least partially fill the filter container 48. The filter material is selected with a pore size such that substantially all of the bone fragments are retained in the filter material.

The filter material may thereby provide physical separation of the bone fragments from the remainder of the material in the aspirate. Such a separation mechanism is referred to as physical separation.

The filter material may also have an affinity for the beneficial components in the aspirate such that as the beneficial components flow past the filter material, the beneficial components are attached to the filter material. The beneficial components are thereby retained in the filter container 48 would be included in the bone graft fabricated therefrom. For example, the filter material may have an affinity for the connective tissue progenitor cells.

In certain embodiments, the filter material is a biomaterial. In other embodiments, the filter material is a naturally occurring biocompatible material. One such biomaterial is solid when dry but that solubilizes when wet. Examples of suitable materials are collagen materials such as are marketed under the designations Helitene and Avitene, which are conventionally used to stop bleeding in wounds. Additional materials could be configured from keratin, collagen, hyaluronic acid, chondroitin, glucosamine, amniotic fluid, tissue from an amniotic sac, or any other biocompatible material that may or may not be hydrogels.

The system also includes a probe 110, which is illustrated in FIGS. 3 and 4. The probe 110 may include a threaded portion 112 and a tip portion 114 at a distal end of the threaded portion 112. The threaded portion 112 has a thread on an outer surface thereof. The tip portion 114 does not have a thread on an outer surface thereof. While not illustrated, a proximal end of the threaded portion 112 may include a chuck portion that facilitates connection of the probe 110 to a drill (not shown).

The threaded portion 112 enhances a flexibility of the probe 110 so that the probe 110 deflects as the probe 110 is extended between the sacrum and the ilium, as described in more detail herein. Such flexing is desirable because the opposing surfaces of the sacrum and the ilium are generally not planar.

The flexibility of the probe 110 enhances the ability of the probe 110 to track the non-planar adjacent surfaces of the ilium and the sacrum so that the probe 110 moves generally between the sacrum and the ilium as opposed to digging into the sacrum and/or the ilium. Such a process facilitates extending the probe 110 further between the sacrum and the ilium as opposed to the tip of the probe 110 cutting into one of the sacrum and/or the ilium.

The tip portion 114 has a generally flat outer surface, as most clearly illustrated in FIG. 4. The length of the tip portion 114 is sufficiently long so that the tip portion 114 tracks along the surface of the sacrum and/or the ilium as opposed to the tip portion 114 digging into the sacrum and/or the ilium.

In certain embodiments, the tip portion 114 has a length that is at least about two times a width of the tip portion 114. In other embodiments, the tip portion 114 has a length that is about four times the length of the tip portion 114.

A distal end 116 of the tip portion 114 is unsharpened. In certain embodiments, the distal end 116 of the tip portion 114 has a blunt surface. In other embodiments, the distal end 116 of the tip portion 114 is semi-spherical.

As used herein, unsharpened means that the distal end 116 of the tip portion 114 does not readily cut through the sacrum and the ilium. Rather, the blunt distal end 116 causes the probe 110 to deflect off of the sacrum and the ilium such that the probe 110 tracks between the sacrum and the ilium.

Figure 5:
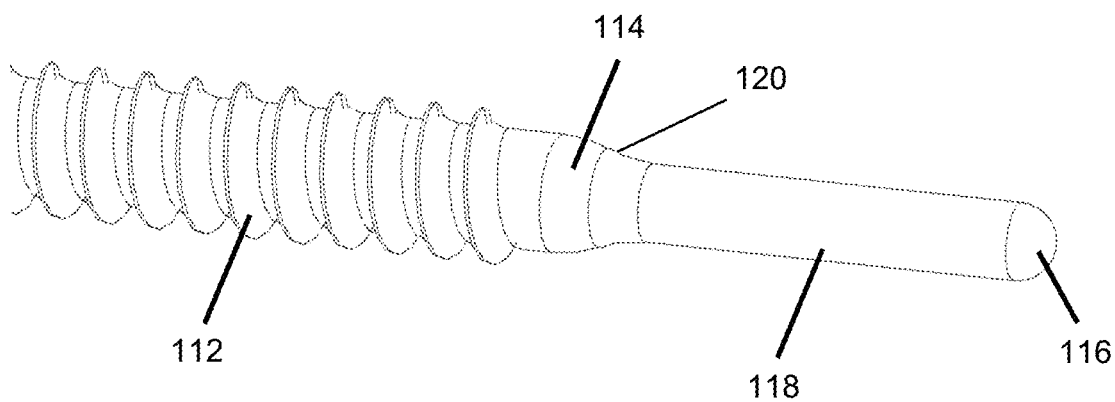
FIG. 5 is an enlarged view of an alternative configuration for a distal end of the probe.

In an alternative configuration of the tip portion 114, which is illustrated in FIG. 5, the tip portion 114 has a reduced diameter section 118 having a diameter that is less than the diameter of the section of the tip portion 114 that is adjacent to the threaded portion 112. Proximate the intersection with the threaded portion 112, the tip portion 114 has a tapered section 120. A diameter of the reduced diameter section 118 is between about 30 percent and about 70 percent of the diameter of the tip portion 114 proximate the threaded portion 112. In certain embodiments, the reduced diameter section 118 is substantially cylindrical.

Figure 6:
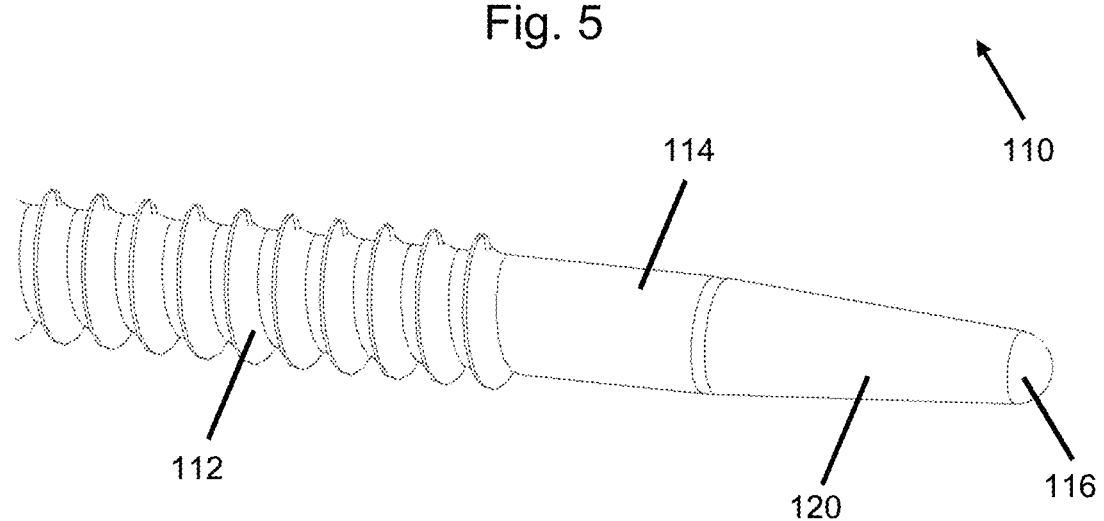
FIG. 6 is an enlarged view of another alternative configuration for a distal end of the probe.

In another alternative configuration of the tip portion 114, which is illustrated in FIG. 6, the tip portion 114 has a tapered section 120 proximate the distal end 116. A diameter of the tapered section 120 proximate the distal end 116 is between about 30 percent and about 70 percent of the diameter of the tip portion 114 proximate the threaded portion 112.

Figure 7:
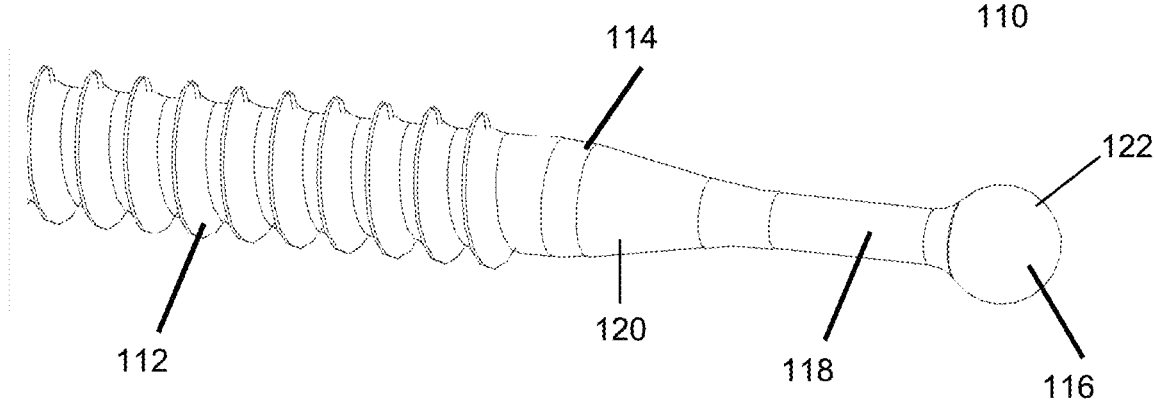
FIG. 7 is an enlarged view of still another alternative configuration for a distal end of the probe.

In still another alternative configuration of the tip portion 114, which is illustrated in FIG. 7, the tip portion 114 has a reduced diameter section 118 having a diameter that is less than the diameter of the section of the tip portion 114 that is adjacent to the threaded portion 112 and is less than a diameter of the distal tip 116. A diameter of the reduced diameter section 118 is between about 30 percent and about 70 percent of the diameter of the distal tip 116. Between the reduced diameter section 118 and the threaded portion 112 is a tapered section 120.

A tip 122 is provided at a distal end of the tip portion 114. The tip 122 has a width that is larger than a width of the reduced diameter section 118. In certain embodiments, the width of the tip 122 is between about 70 percent and about 120 percent of the tip portion 114 proximate the threaded portion 112. In certain embodiments, the tip 122 has a spherical shape.

In use, an incision is made in a patient to provide a lateral access to the sacroiliac joint using a conventionally known technique. The distal end 116 of the probe 110 is placed adjacent to the intersection of the sacrum and the ilium. If necessary, an imaging technique is used to identify the intersection of the sacrum and the ilium.

Figure 9:
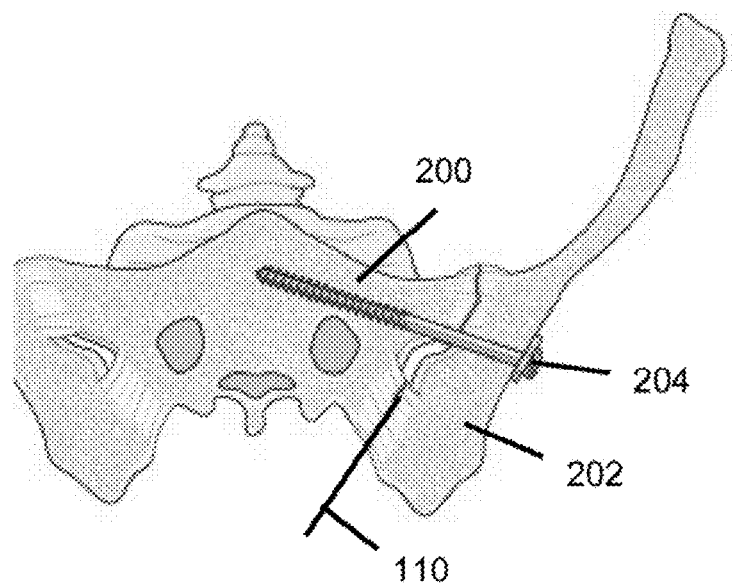
FIG. 9 is a sectional view of the sacroiliac joint taken along a line 9-9 in FIG. 8.

The proximal end of the probe 110 may be attached to a manual or powered driver such as a drill and the drill is used to cause the probe 110 to extend between the sacrum and the ilium as illustrated in FIG. 9. A distance to which the probe 110 is extended between the sacrum and the ilium depends on factors such as the curvature of the sacrum and the ilium in the direction in which the probe 110 is being inserted.

In certain embodiments, the probe 110 is inserted at least about 20 millimeters between the sacrum and the ilium. In other embodiments, the probe 110 is inserted between about 20 millimeters and about 50 millimeters between the sacrum and the ilium.

The probe 110 is advanced in a direction that is generally parallel to the joint line between the sacrum and the ilium. As the probe 110 is being inserted between the sacrum and the ilium, the blunt tip portion 114 causes the probe 110 to follow the path of least resistance through the soft tissue because the blunt tip portion 114 is unable to pierce through the bone.

After the probe 110 is inserted a desired distance between the sacrum and the ilium, the probe 110 is disconnected from the drill. The proximal end of the probe 110 is extended through the aperture 33 at the end of the tip 24 on the harvesting device 12. Depending on the length of the probe 110, the proximal end of the probe 110 may extend through a port 26 in the handle portion 20 of the harvesting device 12 to which the hose 16 is attached.

Movement of the abrading and harvesting device 12 over the probe 110 is continued until the tip portion 24 contacts the sacrum and/or the ilium. At which time, the abrading and harvesting device 12 is rotated in an alternating clockwise and counterclockwise motion. Such rotation of the tip portion 24 against the sacrum and/or the ilium causes the surface thereof to be abraded and/or cut therefrom to produce bleeding bone.

While abrading and/or cutting the sacrum and/or the ilium, the harvesting device 12 may be configured as illustrated in FIG. 1 and a vacuum may be applied to line 15. The vacuum causes bone fragments, liquid and other tissue between the sacrum and the ilium to be withdrawn and collected in the vessel 30.

As the sacrum and/or ilium are abraded and/or cut, the abrading and harvesting device 12 is advanced further between the sacrum and the ilium. This process is continued until the tip portion 24 is proximate the tip portion 114. Thereafter, the probe 110 and the abrading and harvesting device 12 are removed from between the sacrum and the ilium.

A bone growth material may be inserted into the void between the sacrum and the ilium that is formed by the abrading and harvesting device 12. A person of skill in the art will appreciate that a variety of bone growth materials may be utilized in conjunction with the invention. In certain situations, the bone growth material may at least partially be the tissue and bone fragments that are harvested from between the sacrum and the ilium.

While it is possible for the path of the probe 110 to intersect with the path of the aperture formed in the sacrum and the ilium through which the fixation device 130 is extended, it is not required that the path of the probe 110 and the fixation device aperture intersect.

The probe 110 may be extended between the sacrum and the ilium along more than one path. In certain embodiments, the probe 110 is extended between the sacrum and the ilium two or three times. Such a process increases the amount of bleeding bone that is formed between the sacrum and the ilium, which thereby increases the surface area of the fusion and reduces the likelihood of the sacroiliac fusion failing.

In one such embodiment, the probe 110 is oriented so that a first path of the probe 110 may have a length of about 50 millimeters, a second path of the probe 110, which is to the left of the first path, may have a length of about 25 millimeters and a third path of the probe 110, which is to the right of the first path, may have a length of about 25 millimeters.

Pivoting of the probe 110 may be about a pivot point 206 that is proximate a surface of the sacrum 200 and the ilium 202 where the probe 110 begins to extend between the sacrum 200 and the ilium 202. The pivoting of the probe 110 may be along a plane that is generally perpendicular to the plane illustrated in FIG. 9 such that the distal and proximal ends of the probe 110 are alternatively pivoted into and out of the plane illustrated in FIG. 9.

An angle between the first path and the second path may be up to about 45 degrees and an angle between the first path and the third path may be up to about 45 degrees. The channel formed between the sacrum and the ilium may have a diameter that is about the same as the outer diameter of the needle portion 22, which in certain embodiments is about 6 millimeters.

It is possible for at least two of the first path, the second path and the third path to intersect. However, the intersection of the first path, the second path and/or the third path is not a critical feature of the invention.

Figure 8:
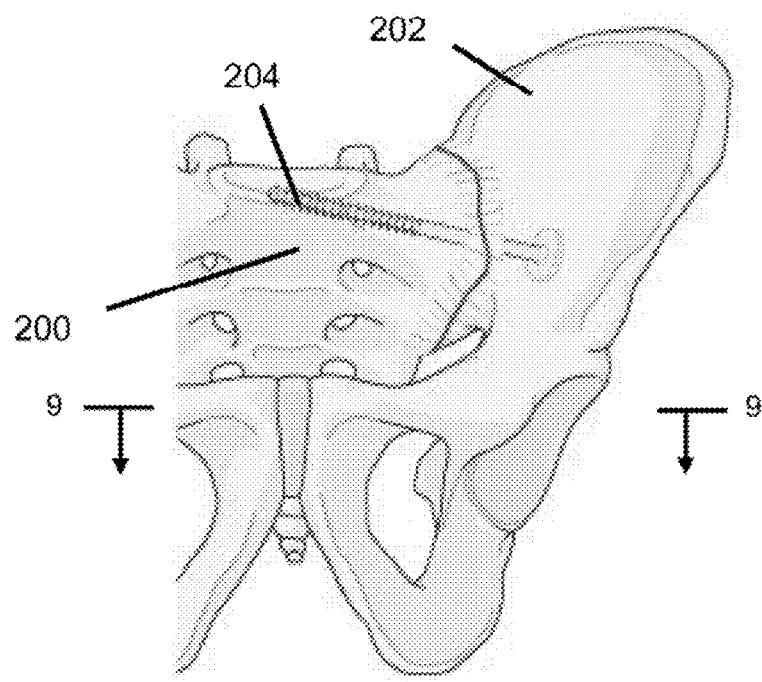
FIG. 8 is a front view of a sacroiliac joint.

FIGS. 8 and 9 illustrate the use of the invention in conjunction with the sacrum 200 and the ilium 202. At least one of the sacrum (first bone) 200 and the ilium (second bone) 202 has an articular surface. At least a portion of the articular surface is non-planar.

FIG. 9 illustrates the probe 110 being extended between the sacrum 200 and the ilium 202. The probe 110 is extended between the first bone and the second bone along the articular surfaces. After the channel is formed with a desired depth, the probe 110 is removed and a bone graft material may be inserted through the needle portion 22 and into the channel.

Thereafter, the needle portion 22 is removed and a fixation device 204 such as a screw or cage is inserted into the sacrum 200 and the ilium 202 to restrict movement of the sacroiliac joint. Alternatively, a bone void filler is inserted into the channel. The bone void filler may have a variety of forms, examples of which include a rigid dowel, compliant demineralized bone matrix or fibers. In still another embodiment, the fixation device and the bone void filler are both used.

While the invention is described with respect to the sacroiliac joint, a person of skill in the art will appreciate that the invention may be utilized in other parts of a human body, examples of which include the foot region and the ankle region.

In the preceding detailed description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The preceding detailed description, therefore, is not to be taken in a limiting sense, and the scope of the present invention is defined by the appended claims.

It is contemplated that features disclosed in this application, as well as those described in the above applications incorporated by reference, can be mixed and matched to suit particular circumstances. Various other modifications and changes will be apparent to those of ordinary skill.

The invention claimed is:

1. A bone fusion system comprising:
a collection vessel;
an abrading and harvesting device comprising:
a needle portion with a central bore extending therethrough, wherein the needle portion has a distal end; and
a sharpened tip attached to the distal end of the needle portion;
tubing operably connecting the collection vessel and the abrading and harvesting device; and
a probe comprising a threaded portion and a tip portion at a distal end of the threaded portion, wherein the threaded portion has a thread on an outer surface thereof, wherein the tip portion is unsharpened and does not have a thread on an outer surface thereof and wherein the probe is extendible through the central bore.

2. The bone fusion system of claim 1, wherein at least part of the needle portion is fabricated from a spiral wound wire that is coated with plastic and wherein at least part of the needle portion has enhanced flexibility.

3. The bone fusion system of claim 1, wherein the collection vessel further comprises a bone fragment collection vessel and wherein the collection vessel is operably attached to a vacuum source.

4. The bone fusion system of claim 1, wherein a distal end of the tip portion has a blunt surface.

5. The bone fusion system of claim 1, wherein the tip portion has a width and a length and wherein the length of the tip portion is about four times the width of the tip portion.

6. The bone fusion system of claim 1, wherein at least part of the tip portion has a reduced diameter.

7. The bone fusion system of claim 6, wherein the part of the tip portion with the reduced diameter is substantially cylindrical.

8. The bone fusion system of claim 6, wherein the part of the tip portion with the reduced diameter decreases in size when moving to a distal end of the tip portion.

9. The bone fusion system of claim 6, and further comprising a tip at a distal end of the tip portion, wherein the tip has a width that is larger than the part of the tip portion with the reduced diameter.

10. The bone fusion system of claim 9, wherein the tip has a spherical shape.

11. A bone fusion system comprising:
a collection vessel;
an abrading and harvesting device comprising:
- a needle portion with a central bore extending therethrough, wherein the needle portion has a distal end and wherein at least part of the needle portion has enhanced flexibility; and
- a sharpened tip attached to the distal end of the needle portion;

tubing operably connecting the collection vessel and the abrading and harvesting device; and
a probe comprising a threaded portion and an unsharpened and unthreaded tip portion, wherein the probe is extendible through the central bore.

12. The bone fusion system of claim 11, wherein at least part of the needle portion is fabricated from a spiral wound wire that is coated with plastic.

13. The bone fusion system of claim 11, wherein the collection vessel further comprises a bone fragment collection vessel and wherein the collection vessel is operably attached to a vacuum source.

14. The bone fusion system of claim 11, wherein a distal end of the tip portion has a blunt surface.

15. The bone fusion system of claim 11, wherein the tip portion has a width and a length and wherein the length of the tip portion is about four times the width of the tip portion.

16. The bone fusion system of claim 11, wherein at least part of the tip portion has a reduced diameter.

17. The bone fusion system of claim 16, wherein the part of the tip portion with the reduced diameter is substantially cylindrical.

18. The bone fusion system of claim 16, wherein the part of the tip portion with the reduced diameter decreases in size when moving to a distal end of the tip portion.

19. The bone fusion system of claim 16, and further comprising a tip at a distal end of the tip portion, wherein the tip has a width that is larger than the part of the tip portion with the reduced diameter.

20. The bone fusion system of claim 19, wherein the tip has a spherical shape.

* * * * *